United States Patent
Brown et al.

(10) Patent No.: US 9,797,885 B2
(45) Date of Patent: Oct. 24, 2017

(54) METHODS AND ARTICLES FOR THE DETECTION OF EXPOSURE TO POLYHYDROXYAROMATIC SKIN IRRITANTS

(71) Applicant: SeeLeaf Inc., Newton, MA (US)

(72) Inventors: Larry Richard Brown, Newton, MA (US); Robert David Feeney, Scituate, MA (US)

(73) Assignee: SeeLeaf Inc., Newton, MA (US)

( * ) Notice: Subject to any disclaimer, the term of this patent is extended or adjusted under 35 U.S.C. 154(b) by 0 days.

(21) Appl. No.: 15/138,133

(22) PCT Filed: Nov. 6, 2014

(86) PCT No.: PCT/US2014/064427
§ 371 (c)(1),
(2) Date: Apr. 25, 2016

(87) PCT Pub. No.: WO2015/069945
PCT Pub. Date: May 14, 2015

(65) Prior Publication Data
US 2016/0327546 A1 Nov. 10, 2016

Related U.S. Application Data

(60) Provisional application No. 61/901,512, filed on Nov. 8, 2013.

(51) Int. Cl.
| | |
|---|---|
| *G01N 33/52* | (2006.01) |
| *G01N 21/78* | (2006.01) |
| *G01N 31/22* | (2006.01) |
| *G01N 33/00* | (2006.01) |

(52) U.S. Cl.
CPC ............ *G01N 33/52* (2013.01); *G01N 21/78* (2013.01); *G01N 31/22* (2013.01); *G01N 33/0098* (2013.01)

(58) Field of Classification Search
CPC ........ G01N 21/77; G01N 21/78; G01N 31/22; G01N 33/0098; G01N 33/52; Y10T 436/20; Y10T 436/203332
USPC ........ 436/127, 131, 164, 169; 422/400, 411, 422/418, 420, 82.05; 514/171
See application file for complete search history.

(56) References Cited

U.S. PATENT DOCUMENTS

| | | | |
|---|---|---|---|
| 3,947,593 A | 3/1976 | Shemano | |
| 4,472,507 A | 9/1984 | Pluim, Jr. | |
| 5,206,118 A | 4/1993 | Sidney | |
| 5,290,068 A * | 3/1994 | Gundjian | B41M 3/142 283/67 |
| 5,310,725 A | 5/1994 | Putsche, Jr. | |
| 5,320,946 A * | 6/1994 | Daniel | C12Q 1/26 435/164 |
| 5,409,908 A | 4/1995 | Sanchez et al. | |
| 6,531,118 B1 | 3/2003 | Gonzalez et al. | |
| 8,389,232 B2 * | 3/2013 | Braslau | A61K 31/69 435/29 |
| 2004/0067590 A1 | 4/2004 | Elhard et al. | |
| 2006/0147341 A1 | 7/2006 | Jangen et al. | |
| 2008/0145948 A1* | 6/2008 | Menon | G01N 21/78 436/164 |
| 2009/0325221 A1* | 12/2009 | Long | A61B 5/14539 435/34 |
| 2010/0248381 A1* | 9/2010 | Hansen | G01N 33/5097 436/131 |
| 2010/0291670 A1* | 11/2010 | Martin | A61L 15/56 435/287.9 |
| 2011/0300635 A1 | 12/2011 | Menon | |

OTHER PUBLICATIONS

Parke, Donna. Applied and Environmental Microbiology, Aug. 1992, pp. 2694-2697.*

* cited by examiner

*Primary Examiner* — Maureen Wallenhorst
(74) *Attorney, Agent, or Firm* — Radha Iyengar

(57) ABSTRACT

A method, an article and a kit for the detection and visual indication of contact with or exposure to a polyhydroxyaromatic skin irritant found in the sap of a plant is provided herein. The article incorporates a colorless leuco dye that undergoes an instantaneous visible color change when contacted with or exposed to a polyhydroxyaromatic skin irritant in the sap of a plant or on a subject. This color change is an indication that contact with or exposure to a polyhydroxyaromatic skin irritant has occurred. Polyhydroxyaromatic skin irritants found in the sap of plants include those found in poison ivy, poison oak, poison sumac, poison dogwood, mango tree, cashew tree and lacquer tree. The leuco dye of the invention is Pergascript Red I-6B (1(3H)-isobenzofuranone,3,3-bis(2-methyl-1-octyl-1H-indol-3-yl)-).

8 Claims, No Drawings

METHODS AND ARTICLES FOR THE DETECTION OF EXPOSURE TO POLYHYDROXYAROMATIC SKIN IRRITANTS

RELATED APPLICATIONS

This application is a U.S. National Phase application, filed under 35 U.S.C. §371, of International Application No. PCT/US2014/064427, filed Nov. 6, 2014, which claims the benefit of and priority to U.S. Provisional Application No. 61/901,512, filed Nov. 8, 2013. The contents of each of these applications are hereby incorporated by reference in their entireties.

BACKGROUND OF THE INVENTION

A hazard traditionally associated with outdoor activities such as gardening, hiking and camping has been the possibility of exposure to polyhydroxyaromatic skin irritants commonly found in plants such as, poison ivy, poison oak, poison sumac, and the like. The sap of such plants can cause an allergic reaction upon contact with the skin, despite the fact that the polyhydroxyaromatic skin irritant naturally occurs in low concentrations (e.g., 2-5% of the sap) and the contact is usually brief and incidental. The extent of reaction varies from individual to individual. Some individuals may experience little or no reaction or simply some itching which disappears after a few days, while others develop a severe skin rash which may require treatment with prescription antibiotics and/or prescription steroids and may need several weeks or even months to fully heal. Occasionally, exposure can lead to nephropathy and even to fatal systemic anaphylaxis.

The most common approach to this problem has been to avoid any contact with plants that contain the polyhydroxyaromatic skin irritants, which approach is extremely practical but not always workable under the circumstances. The leaves of poison ivy, poison oak or poison sumac for example, are similar to the foliage of other harmless plants and thus may not be readily distinguishable. The challenges to even skilled workers in the outdoors in identifying these plants is exemplified by the observation that 10% of lost work hours in the United States Forestry services is attributed to exposure to these poison plants. Various medications available for treating the effects of contact with plants that contain polyhydroxyaromatic skin irritants include a course of topical and/or enteric treatments with hydrocortisones, betamethasone, and other similar corticosteroids. Repeated exposure to the polyhydroxyaromatic skin irritants can result in a severe hypersensitive immunoreaction, that is often extremely painful and, occasionally, fatal.

Early treatment after exposure to the polyhydroxyaromatic skin irritant, that is before the onset of symptoms, is desirable. However, such treatment is predicated upon knowing that actual contact with the polyhydroxyaromatic skin irritant found in plants has occurred. Unfortunately contact with a polyhydroxyaromatic skin irritant does not result in an immediate skin irritation as one typically does not realize having been exposed to a polyhydroxyaromatic skin irritant until the symptoms develop some time after contact. It is not uncommon for the first symptom, typically itching, to manifest itself between about 6 hours and about 24 hours after contact. Additional symptoms, such as redness and swelling may not occur for up to 48 hours after contact, followed eventually by the formation of microblisters. There is a need to develop methods to promptly detect exposure to a polyhydroxyaromatic skin irritant found in the sap of plants.

There is a need in the art for new and more effective compositions and methods to promptly detect exposure to a polyhydroxyaromatic skin irritant found in the sap of plants. The invention is directed to these, as well as other, important ends.

SUMMARY OF THE INVENTION

The present invention provides for a method, an article and a kit for the detection and visual indication of contact with or exposure to a polyhydroxyaromatic skin.

One embodiment of the invention features a method for detecting contact with or exposure to a polyhydoxyaromatic skin irritant found in the sap of a plant by contacting an article comprising a leuco dye with the polyhydroxyaromatic skin irritant wherein the leuco dye undergoes an instantaneous color change. This visually observable color change of the leuco dye serves as an indicator that exposure to a polyhydroxyaromatic skin irritant has occurred. In some embodiments the article comprises a colorless leuco dye that undergoes an instantaneous color change to a colored form of the leuco dye on contact with the polyhydroxyaromatic skin irritant.

Another embodiment of the invention provides for an article comprising a leuco dye used for the detection of contact with or exposure to a polyhydoxyaromatic skin irritant found in the sap of a plant. In this embodiment of the invention the article comprising a leuco dye undergoes an instantaneous color change when the leuco dye in the article comes in contact with or is exposed to a polyhydoxyaromatic skin irritant found in the sap of plants. This visually observable color change of the leuco dye impregnated in the article serves as an indicator that contact with or exposure to a polyhydroxyaromatic skin irritant has occurred. In certain embodiments the article comprises a colorless leuco dye that undergoes an instantaneous color change to a colored form of the leuco dye on contact with the polyhydroxyaromatic skin irritant.

Yet another embodiment of the invention features a kit for detecting the presence of a polyhydroxyaromatic skin irritant found in the sap of plants. The kit comprises an article comprising a leuco dye and a set of instructions of how to use the kit, wherein the kit is used for the detection of contact with or exposure to a polyhydroxyaromatic skin irritant found in the sap of plants. In this embodiment of the invention the article comprising the leuco dye undergoes an instantaneous color change when the leuco dye in the article comes in contact with a polyhydoxyaromatic skin irritant found in the sap of plants.

In one embodiment of the invention the polyhydroxyaromatic skin irritant found in the sap of plants is from the genus Toxicondedron of the Anacardiaceae family. In this embodiment the polyhydroxyaromatic skin irritant found in the sap of plants contains at least one urushiol compound which often irritates exposed skin.

In another embodiment of the invention the leuco dyes are Pergascript Red I-6B, Pergascript Green I-2G, Copikem I, Copikem 35 Magenta or Copikem 4 Black.

In another embodiment of the invention the leuco dyes is Pergascript Red I-6B.

In one embodiment, the invention is a kit comprising the elements disclosed herein and a set of instructions on how to use the kit, wherein the kit is used for detecting exposure to or contact with a polyhydroxyaromatic skin irritant. The kit can be used, for example, in the home, in the field, in a camp, in a clinic, in a hospital, in an emergency room, and the like.

DETAILED DESCRIPTION OF CERTAIN PREFERRED EMBODIMENTS OF THE INVENTION

As used throughout the disclosure, the following terms, unless otherwise indicated, shall be understood to have the following meanings.

Definition/Terminology

The use of the articles "a", "an", and "the" in both the following description and claims are to be construed to cover both the singular and the plural, unless otherwise indicated herein or clearly contradicted by context. The terms "comprising", "having", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of."

"Leuco dye" as used herein refers to a dye whose molecules can acquire two forms, one of which is colorless. The leuco dye on contact with a polyhydroxyaromatic skin irritant undergoes a distinct color change. In one embodiment of the invention on contact with a polyhydroxyaromatic skin irritant the color of the leuco dye changes from a colorless form to a colored form.

"Subject" or "individual" is used to define any person or animal that may have contacted, or has the potential to contact or to be exposed to a polyhydroxyaromatic skin irritant. Person includes males and females.

Polyhydroxyaromatic Skin Irritants

The present invention relates to methods for detecting the presence of or methods for detecting the exposure to or contact with a polyhydroxyaromatic skin irritant commonly found in the sap of plants known to cause skin irritations, such as contact dermatitis. These plants, typically from the genus Toxicondendron of the Anacardiaceae family, contain at least one urushiol compound which often irritates exposed skin. For example, contact with the sap or oils of poison ivy, poison oak, poison sumac, poison dogwood, lacquer trees, mango trees, and cashew trees, is known to cause contact dermatitis. In one embodiment, the present invention provides a point of contact test that may be used by an untrained user in the field. Field use may also provide the user with immediate results, allowing the user to take preventative measures to avoid developing contact dermatitis, such as washing the point of contact or changing clothes, in the event of a positive response indicating actual exposure to polyhydroxyaromatic skin irritants.

In another embodiment of the invention the polyhydroxyaromatic skin irritant is found in the sap of a plant, such as, for example, *Toxicodendron diversilobum* (poison oak), *Toxicodendron radicans* (poison ivy), *Toxicodendron rydbergii* (Rocky Mountain poison oak), *Toxicodendron vernix* (poison sumac or poison dogwood), *Toxicodendron vernicifluum*, (Japanese or Asian lacquer tree), *Magnifera indica* (mango tree), *Anacardium occidentale* (cashew tree) *Gluta renghas* (Rengas tree), *Melanorrhoea usitata* (Burmese lacquer tree), *Metopium toxiferum* or *Comocladia dodnaea* (both Caribbean shrubs), *Semecarpus acardium* (India marking nut tree), *Ginkgo biloba*, or a member of the Proteaceae family.

In yet another embodiment of the invention the polyhydroxyaromatic skin irritant found in the sap or oil of a plant is an urushiol compound, and is a mixture of substituted catechols (polyhydroxyaromatic compounds) of Formula A:

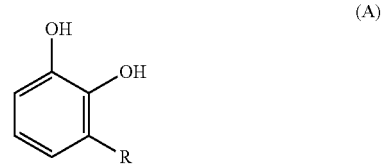

(A)

wherein:
I $R=(CH_2)_{14}CH_3$
II $R=(CH_2)_7CH=CH(CH_2)_5CH_3$
III $R=(CH_2)_7CH=CHCH_2CH=CH(CH_2)_2CH_3$
IV $R=(CH_2)_7CH=CHCH_2CH=CHCH=CHCH_3$
V $R=(CH_2)_7CH=CHCH_2CH=CHCH_2CH=CH_2$ Poison ivy, *Toxicodendron radicans*, and poison oak *Toxicodendron. diversolobum* urushiols comprise primarily a mixture of 15 carbon side-chains catechols or pentadecylcatechols of Formula (A), Poison oak urushiol also contains 17 carbon side-chains catechols or heptadecylcatechols of the $C_{17}H_{35}$ series, varying in saturation down to the $C_{17}H_{29}$ species. The aliphatic hydrocarbon side group of the catechol compound allows bonding to, and penetration of, the skin. The hydrocarbon side chain is hydrophobic, and the dihydroxy phenyl moiety is hydrophilic. The likelihood and severity of allergic reaction to urushiol is dependent on the degree of unsaturation of the alkyl chain.

In one embodiment the polyhydroxyaromatic skin irritant is an urushiol compound found in a plant and the invention provides methods for its rapid detection by use of visual indications.

In another embodiment the polyhydroxyaromatic skin irritant comprise urushiol compounds found in poison ivy (*Toxicodendron radicans*) and poison oak (*Toxicodendron. Diversolobum*) and the invention provides methods for their rapid detection by use of visual indications.

In yet another embodiment the invention provides methods to detect the presence of or exposure to catechols and alkyl-substituted catechols, such as, for example, urushiol, catechin, epicatechin, gallocatechin, epigallocatechin, epigallocatechin-3-gallate, and the like; and chatecholamines, such as, for example, epinephrine, norepinephrine, dopamine, dihydroxyphenylalanine (DOPA), and the like. In one embodiment the catechol is urushiol.

In yet another embodiment the invention provides methods to detect the presence of or exposure to monohydroxyaromatic compounds.

Leuco Dyes

The present invention comprises a leuco dye capable of a perceivable change, when contacted with a polyhydroxyaromatic skin irritant. Any leuco dye may be used in the present invention.

Specific leuco dyes suitable for use in the present invention include, but are not limited to, fluorans, phthalides, acylluecoazine dyes, leucoauramine dyes, spiropyrane dyes, rhodaminelactam dyes, triarylmethane dyes, amino-triarylmethanes, aminoxanthenes, aminothioxanthenes, amino-9, 10-dihydro-acridines, aminophenoxazines, aminophenothiazines, aminodihydro-phenazines, aminodiphenylmethanes, aminohydrocinnamic acids (cyanoethanes, leuco methines) and corresponding esters, 2(p-hydroxyphenyl)-4,5-diphenylimidazoles, indanones, leuco indamines, hydrozines, leuco indigoid dyes, amino-2,3-dihydroanthraquinones, tetrahalo-p,p'-biphenols, 2(p-hydroxyphenyl)4,5-diphenylimidazoles, phenethylanilines, chromene dyes and combinations of two or more thereof.

In one embodiment of the invention, the leuco dye can be a fluoran, an aminotriarylmethane, a phthalide, such as for example, a diarylphthalide dye, an indolyphthalide dye or a combination of two or more thereof. Suitable fluoran based leuco dyes include, but are not limited to, 3-diethylamino-6-methyl-7-anilinofluorane, 3-(N-ethyl-p-toluidino)-6-methyl-7-anilinofluorane, 3-(N-ethyl-N-isoamylamino)-6-methyl-7-anilinofluorane, 3-diethylamino-6-methyl-7-(o,p-dimethylanilino)fluorane, 3-pyrrolidino-6-methyl-7-anilinofluorane, 3-piperidino-6-methyl-7-anilinofluorane, 3-(N-cyclohexyl-N-methylamino)-6-methyl-7-anilinofluorane, 3-diethylamino-7-(m-trifluoromethylanilino)fluorane, 3-dibutylamino-6-methyl-7-anilinofluorane, 3-diethylamino-6-chloro-7-anilinofluorane, 3-dibutylamino-7-(o-chloroanilino)fluorane, 3-diethylamino-7-(o-chloroanilino)fluorane, 3-di-n-pentylamino-6-methyl-7-anilinofluoran, 3-di-n-butylamino-6-methyl-7-anilinofluoran, 3-(n-ethyl-n-isopentylamino)-6-methyl-7-anilinofluoran, 3-pyrrolidino-6-methyl-7-anilinofluoran, 1 (3H)-isobenzofuranone,4,5,6,7-tetrachloro-3,3-bis[2-[4-(dimethylamino)phenyl]-2-(4-methoxyphenyl)ethenyl], and combinations of two or more thereof. Suitable aminotriarylmethane leuco dyes include, but are not limited to, tris(N,N-dimethylaminophenyl) methane (LCV); deutero-tis(N,N-dimethylaminophenyl)methane (D-LCV); tris(N,N-diethylaminophenyl) methane(LECV); deutero-tris(4-diethylaminolphenyl) methane (D-LECV); tris(N,N-di-n-propylaminophenyl) methane (LPCV); tri s(N,N-di-n-butylaminophenyl) methane (LBCV); bis(4-diethylaminophenyl)-(4-diethylamino-2-methyl-phenyl) methane (LV-1); bis(4-diethylamino-2-methylphenyl)-(4-diethylamino-phenyl) methane (LV-2); tris(4-diethylamino-2-methylphenyl) methane (LV-3); deutero-bis(4-diethylaminophenyl)-(4-diethylamino-2-methylphenyl) methane (D-LV-1); deutero-bis(4-diethylamino-2-methylphenyl)(4-diethylaminophenyl) methane (D-LV-2); bis(4-diethylamino-2-methylphenyl)(3,4-dimethoxyphenyl) methane (LB-8); aminotriarylmethane leuco dyes having different alkyl substituents bonded to the amino moieties wherein each alkyl group is independently selected from $C_1$-$C_4$ alkyl; and aminotriaryl methane leuco dyes with any of the preceding named structures that are further substituted with one or more alkyl groups on the aryl rings wherein the latter alkyl groups are independently selected from $C_1$-$C_3$ alkyl. Suitable leuco dyes are described more fully in the literature, such as in U.S. Pat. No. 3,658,543, U.S. Pat. No. 6,124,377, U.S. Pat. No. 6,251,571, U.S. Pat. No. 6,958,181, U.S. Pat. No. 7,270,865 and U.S. Pat. No. 7,329,630, U.S. Pat. No. 5,476,830, U.S. Pat. No. 7,122,247 and WO 2007/123966, the disclosures of each of which are incorporated herein by reference in their entirety.

In another embodiment of the invention the leuco dyes include, but are not limited to, those listed in Table I.

TABLE 1

| Trade name* | CAS # | Chemical name |
| --- | --- | --- |
| Pergascript Red I 6B | 50292-95-0 | 1(3H)-Isobenzofuranone,3,3-bis(2-methyl-1-octyl-1H-indol-3-yl)- |
| Pergascript Blue S-RB | 67707-04-4 | Benzenamine, 4,4'-[(9-butyl-9H-carbazol-3-yl)methylene]bis[N-methyl-N-phenyl- |
| Pergascript Black N-102 | 29512-49-0 | 2-Anilino-3-methyl-6-diethylaminofluoran |
| Pergascript Green I-2G; Copikem 5; Copikem 5 Grape; Copikem 5 Green | 34372-72-0 | Spiro[isobenzofuran-1(3H),9'-[9H]xanthen]-3-one,2'-[bis(phenylmethyl)amino]-6'-(diethylamino)- |
| Pergascript Blue I-2G | 87563-89-1 | 7-[4-(diethylamino)-2-ethoxyphenyl]-7-(2-methyl-1-octyl-1H-indol-3-yl)-Furo[3,4-b]pyridin-5(7H)-one |
| Copikem I Crystal Violet Lactone | 1552-42-7 | 1(3H)-Isobenzofuranone,6-(dimethylamino)-3,3-bis[4-(dimethylamino)phenyl]- |
| COPIKEM ® 747 Red | 26628-47-7 | Spiro(12H-benzo(a)xanthene-12,1'(3'H)-isobenzofuran-3'-one,9-(diethylamin-o) |
| COPIKEM ® 35 magenta | 50292-91-6 | 3-[Butyl-2-methylindol-3-yl]-3-(1-octyl-2-methylindol-3-yl)-1(3H)isobenzofuranone |
| COPIKEM ® 34 Black | 89331-94-2 | 2'-phenylamino-3'-methyl-6'-(dibutylamino)spiro isobenzofuran-1(3H),9'-(9H)-xanthen)-3-one |
| COPIKEM ® 14 Orange | 67697-75-0 | 3-[bis (4-octylphenyl)amino]-3-[4-(dimethylamino)phenyl]phthalide |
| COPIKEM ® 4 Black | 29512-49-0 | 3-diethylamino-6-methyl-7-anilinofluoran |
| COPIKEM ® 16 Magenta | 50292-98-3 | 3,3-bis(1-octyl-2-methyl-1H-indol-3-yl)-1-[3H]-isobenzofuranone |
| COPIKEM ® 7 Grape | 92453-31-1 | 3-(1(3H)-Isobenzofuranone, 3-(1-Butyl-2-Methyl-1H-Indol-3-YL)-6-(Dimethylamino)-3-[4-(Dimethylamino) Phenyl] |
| COPIKEM ® 4 Black | 29512-49-0 | 3-diethylamino-6-methyl-7-anilinofluoran |
| COPIKEM ® 16 Magenta | 50292-95-0 | 3,3-bis(1-octyl-2-methyl-1H-indol-3-yl)-1-[3H]-isobenzofuranone |
| COPIKEM ® 20 Magenta | 50292-91-6 | 3,3-bis(1-butyl-2-methyl-1H-indol-3yl)-1-[3H]-isobenzofuranone |
| COPIKEM ® 35 Magenta | 50292-91-6 | 3-[Butyl-2-methylindol-3-yl]-3-(1-octyl-2-methylindol-3-yl)-1(3H)isobenzo-furanone, |

*Trade names are those of BASF and Hilton Davis

In yet another embodiment of the invention, the leuco dyes are Pergascript Red I-6B, Pergascript Green I-2G, Copikem I, Copikem 35 Magenta and Copikem 4 Black. These leuco dyes are colorless and undergo an instantaneous visible color change to a colored form on contact with a polyhydroxyaromatic skin irritant. The intensity of the color is dependent on the concentration of the polyhydroxyaromatic skin irritant.

In another embodiment of the invention the leuco dye is Pergascript Red I-6B.

Although a wide range of concentrations for the color-forming leuco dyes are suitable for use in the present invention, concentrations of at least about 0.001 wt. % to 5 wt. % or more are useful. Concentrations on the order of 0.01 wt. % to 0.5 wt. %, 0.02 to 0.2 wt. % and 0.03 to 0.1 wt. % are more typical. These ranges are only exemplary and other weight ranges can be used, depending on the desired image characteristics and other considerations.

In another embodiment of the invention, the leuco dyes of the present invention which undergo a visible color change when reacted with the polyhydroxyaromatic skin irritant compounds can be used in combination with another compound that also results in a visible color change when reacted with the polyhydroxyaromatic skin irritant. These compound include, but are not limited to, metal salts, such as ferric salts, salts of chromium, silver, and copper, diazammonium salts, 4-amino-antipyrine, and/or 2,6-dibromo-quinone-4-chlorimide and combinations of two or more thereof. In another embodiment, the compound that also results in a visible color change may be selected from the group consisting of: ferric citrate, ferric chloride, and ferric nitrate and combinations of two or more thereof.

Article

Leuco dyes of the present invention may be applied to an article to detect the presence of or exposure to a polyhydroxyaromatic skin irritant found in the sap of a plant. The leuco dye may be deposited on a surface of the article, and/or deposited throughout the article, such as by immersing the article in a solution containing a leuco dye The article may be comprised of any material having a surface suitable for carrying a leuco dye. Examples of suitable articles include, but are not limited to, a polymer sheet, a fibrous sheet, a fabric, a sponge, a gauze, a swab, a gel, a foam, a wipe, a tattoo, a natural or synthetic woven or nonwoven material, clothing, a liquid, a gel, a paste, an aerosol or a substrate, such as a strip of paper, cloth or foamed plastic, and the like.

The article may be configured to be removably attachable to a subject. The article containing a leuco dye may be positioned upon the subject, thereby coming into direct contact with area vegetation, allowing the leuco dye in the article to undergo an instantaneous color change. The article may be directly and/or indirectly attached to the subject. The article may be configured to be removably attachable to an article worn by the subject, such as sock, shoe, shoe cover, pants, shorts, shirt, collar, shoe lace, ankle band, wrist band, bandana, and the like. The article may also be configured to be removably attachable directly to the subject's skin or to an animal's fur.

The article need not be worn, but may be configured to be used by a subject after potential exposure to polyhydroxyaromatic skin irritants contained in plants, or for direct identification of plants containing polyhydroxyaromatic skin irritants. For example, the article may be configured to be used as a wipe, which may be used to detect polyhydroxyaromatic skin irritant compounds that have come into contact with the subject and may be used to sample a number of different surfaces with one article. A single wipe type article may be contacted with the skin of the legs, arms, and hands as well as with clothing worn by the individual. Similarly, the wipe type article may be contacted with the collar, bandana, and legs of an animal, and the like, and with inanimate objects such as, for example, a bicycle, garden tool, golf club, metal detector, automobile steering wheel, and the like. The use of a wipe type article allows an individual to examine a larger area of potential contact with polyhydroxyaromatic skin irritants than a stationary article that is worn in one location. The ability to examine a number of different surfaces to produce a single point reaction may result in a more representative indication of exposure to polyhydroxyaromatic skin irritants. The article may be, but need not be, reusable in the event that a previous use indicated that polyhydroxyaromatic skin irritants are not present and therefore no color change was detected. A positive indication of the presence of polyhydroxyaromatic skin irritants affords the subject the opportunity to take preventative measures, such as washing the point of contact and/or changing clothing and/or prophylactic treatment with medication.

The article may be a liquid, a gel, a paste, an aerosol or a substrate, such as a strip of paper, a cloth, a tattoo or a foamed plastic. The article may, but need not, be moistened by a liquid, a gel or a foam. The article may be saturated with water. The article may be in a dry form i.e. does not containing any excess liquid. The liquid may be any liquid or solution that aids in the removal of polyhydroxyaromatic skin irritants from the surface of the subject and in the transfer of the polyhydroxyaromatic skin irritants to the surface of the article for reaction with the leuco dye present in the article. The liquid may be solvent or water based. In one embodiment, the leuco dye in a water miscible solvent such as ethanol, isopropyl alcohol or acetone is applied to the article.

The leuco dye of the present invention undergoes an instantaneous visible color change by reacting with polyhydroxyaromatic skin irritant compounds present in the sap of plants thereby alerting the subject to the presence of a polyhydroxyaromatic skin irritant. The leuco dye maybe present in a dry form in the article of use The leuco dye may be in a liquid carrier that may be applied to the article, the surface of a subject, and/or directly a surface of a plant. The liquid containing the leuco dye may be applied to the various surfaces by conventional methods, such as by droplet, immersion, brush, roller, spray, and the like. The liquid may, but need not, assist in solubilzing the polyhydroxyaromatic skin irritant compounds, and may be water or solvent based. In one embodiment, the liquid carrier is selected to wet both the surface of the article and the leuco dye. In one embodiment, the liquid carrier is a water miscible solvent such as ethanol, isopropyl alcohol or acetone.

In accordance with the invention, the article comprising the leuco dye serves as an indicator which can be worn for detecting and signaling, through a visually observable color change, on contact with the polyhydroxyaromatic skin irritant. The leuco dye impregnated in the article provides a chemical reactant which promptly reacts and darkens upon contact in a natural environment with a naturally occurring concentration of the polyhydroxyaromatic skin irritant found in the sap of the plants.

In other embodiments, the color changing leuco dye can be included in liquid gels, creams, a tattoo and the like, and applied to the skin or to clothing. For example, the leuco dye may be sprayed on, applied as an oil or cream, etc. In this embodiment when the leuco dye comes in contact with or is exposed to the polyhydroxyaromatic skin irritant it undergoes an instantaneous visible color change.

In another embodiment, the invention provides for a chemical spray that can be used in the field to allow the detection of polyhydroxyaromatic skin irritants. The chemical spray comprising the leuco dye undergoes an instantaneous visible color change when contacted with a plant containing a polyhydroxyaromatic skin irritant.

From the foregoing, it will thus be apparent that the present invention comprises a method or technique for the rapid detection of contact with or exposure to polyhydroxyaromatic skin irritants found in the sap of plants. The articles described herein comprising the leuco dye are inexpensive, easy to manufacture and utilize a chemical reactant which provides a positive, reliable indication of contact with or exposure to polyhydroxyaromatic skin irritants so that preventative measures can be undertaken immediately to minimize the allergic reaction which usually occurs following contact with plants containing polyhydroxyaromatic skin irritants.

Detection of Color Chance

The color change of an article comprising a leuco dye changes after exposure to a polyhydroxyaromatic skin irritant may be determined either visually or by using instrumentation. In its simplest form, the article comprising a leuco dye can change color upon exposure to the polyhydroxyaromatic skin irritant in a manner that is readily visible to the wearer and/or caregiver without the need for any visual aid or other instrumentation. Typically a visual change in color of >5 ΔE most humans can visually see changes in color (color 1 to color 2) or increase or decrease of the same shade of color.

In other embodiments, the color intensity resulting from the change in color of the article comprising a leuco dye after exposure to the polyhydroxyaromatic skin irritant can be measured with an optical reader. The actual configuration and structure of the optical reader may generally vary as is readily understood by those skilled in the art. Typically, the optical reader contains an illumination source that is capable of emitting electromagnetic radiation and a detector that is capable of registering a signal (e.g., transmitted or reflected light). The illumination source may be any device known in the art that is capable of providing electromagnetic radiation, such as light in the visible or near-visible range (e.g., infrared or ultraviolet light). For example, suitable illumination sources that may be used in the present invention include, but are not limited to, light emitting diodes (LED), flash lamps, cold-cathode fluorescent lamps, electroluminescent lamps, and the like. The illumination may be multiplexed and/or collimated. In some embodiments, the illumination may be pulsed to reduce any background interference. Further, illumination may be continuous or may combine continuous wave (CW) and pulsed illumination where multiple illumination beams are multiplexed (e.g., a pulsed beam is multiplexed with a CW beam), permitting signal discrimination between a signal induced by the CW source and a signal induced by the pulsed source. For example, in some embodiments, LEDs (e.g., aluminum gallium arsenide red diodes, gallium phosphide green diodes, gallium arsenide phosphide green diodes, or indium gallium nitride violet/blue/ultraviolet (UV) diodes) are used as the pulsed illumination source.

The detector may generally be any device known in the art that is capable of sensing a signal. In one embodiment, the detector may be an electronic imaging detector that is configured for spatial discrimination. Some examples of such electronic imaging sensors include, but are not limited to, high speed, linear charge-coupled devices (CCD), charge-injection devices (CID), complementary-metal-oxide-semiconductor (CMOS) devices, and the like. Such image detectors, for instance, are generally two-dimensional arrays of electronic light sensors, although linear imaging detectors (e.g., linear CCD detectors) that include a single line of detector pixels or light sensors, such as, for example, those used for scanning images, may also be used. Each array includes a set of known, unique positions that may be referred to as "addresses." Each address in an image detector is occupied by a sensor that covers an area (e.g., an area typically shaped as a box or a rectangle). This area is generally referred to as a "pixel" or pixel area. A detector pixel, for instance, may be a CCD, CID, or a CMOS sensor, or any other device or sensor that detects or measures light. The size of detector pixels may vary widely, and may in some cases have a diameter or length as low as 0.2 micrometers.

In other embodiments, the detector may be a light sensor that lacks spatial discrimination capabilities. Suitable examples of such light sensors include, but are not limited to, photomultiplier devices, photodiodes, such as avalanche photodiodes or silicon photodiodes, and the like. Silicon photodiodes are sometimes advantageous in that they are inexpensive, sensitive, capable of high-speed operation (short rise time/high bandwidth), and easily integrated into most other semiconductor technology and monolithic circuitry. In addition, silicon photodiodes are physically small, which enables them to be readily incorporated into various types of detection systems. If silicon photodiodes are used, then the wavelength range of the emitted signal may be within their range of sensitivity, which is 400 to 1100 nanometers.

Optical readers may generally employ any known detection technique, including, for instance, luminescence (e.g., fluorescence, phosphorescence, etc.), absorbance (e.g., fluorescent or non-fluorescent), diffraction, etc. In one particular embodiment of the present, the optical reader measures color intensity as a function of absorbance.

The optical reader can be, in one embodiment, utilized as a portable monitor to be easily monitored by the wearer and/or caregiver. For example, the optical reader can be interfaced with the article comprising a leuco dye and can provide a signal (e.g., via a wired connection or wireless connection) to a display unit. The display unit can then alert the wearer and/or caregiver that the presence of the polyhydroxyaromatic skin irritant has (or has not) been detected. In addition the location of the polyhydroxyaromatic skin irritant can be mapped on a GPS device such as, for example a smart phone.

Kits

The invention provides kits for detecting the presence of a polyhydroxyaromatic skin irritant found in the sap of plants. The kit comprises an article comprising a leuco dye and a set of instructions of how to use the kit, wherein the kit is used for the detection of or exposure to a polyhydroxyaromatic skin irritant found in the sap of plants. In this embodiment of the invention the article comprising the leuco dye undergoes an instantaneous color change when the leuco dye in the article comes in contact with a polyhydoxyaromatic skin irritant found in the sap of plants. The kit may optionally contain an article to removing the skin irritant from the skin, such as, for example, a wipe, an alcohol wipe, a wipe comprising a solvent to solubilize and remove the polyhydroxy aromatic skin irritant, and the like, The kits of the invention include, but are not limited to wipes, sprays, gels, liquids, foams, and the like. For example, a liquid containing the leuco dye may be applied by conventional methods, such as by droplet, immersion, brush, roller, spray, and the like, to various surfaces that might have been in contact with a polyhydroxyaromatic skin irritant. The liquid comprising the leuco dye would undergo an instantaneous color change thereby acting as a detector for the polyhydroxyaromatic skin irritants.

These kits may be used by clinicians, nursing staff, paramedics, emergency rescue team members, the military, firefighters, forestry personnel, lumber workers, hunters, mountaineers, hikers, anglers, gardeners, and the like. The kit can be used, for example, in the home, in the field, in a camp, in a clinic, in a hospital, in an emergency room, and the like.

The invention having now been described by way of written description, those of skill in the art will recognize that the invention can be practiced in a variety of embodiments and that the foregoing description and examples below are for purposes of illustration and not limitation of the claims that follow.

EXAMPLES

General Information

2-Deoxy urushiol, technical grade, 90% purity (3-pentadecylphenol) was purchased from Sigma-Aldrich (catalog number P4402, lot 05618BJV, CAS number 501-24-6).

Pergascript Red I-6B (BASF) and Pergascript Green I-2G (BASF) were obtained from BASF, Suffolk, Va., Copikem I (Hilton Davis), Copikem 35 Magenta (Hilton Davis) and Copikem 4 Black (Hilton Davis) were obtained from Hilton Davis, Cincinnati, Ohio Poison oak extract was obtained from Alfred Del Grosso, Ph.D., Laboratory of Analytical Chemistry, Food and Drug Administration, Rockville, Md.

Sodium carbonate (Arm & Hammer, Princeton, N.J.) was purchased from Stop and Shop Supermarket.

Canvas gloves was purchased from ULINE (catalog number S-13462).

Example 1

Several different leuco dyes were tested to determine if they would undergo a visible color change when contacted with or exposed to an urushiol containing compound. 2-deoxy urushiol was heated in a polypropylene test tube to 50° C. in a water bath to form a free flowing liquid. The free flowing 2-deoxy urushiol liquid was then combined with a white leuco dye and the color change recorded. The results are shown in Table 2.

TABLE 2

| Leuco dye | Initial color | Color after exposure to 2-deoxy urushiol |
| --- | --- | --- |
| Pergascript Red I-6B | White | Red, Magenta |
| Pergascript Green I-2G | White | Green |
| Copikem I | White | Blue |
| Copikem 35 Magenta | White | Magenta |
| Copikem 4 Black | White | Black |

As shown in Table 2, all five leuco dyes tested underwent a visible color change upon contacted with an urushiol containing compound.

Example 2

Each of the following five powdered leuco dyes, Pergascript Red-I-6B, Pergascript Green I-2G, Copikem I, Copikem 35 Magenta and Copikem 4 Black were tested separately for evidence of a visible color change after exposure to vegetation known to contain poison ivy.

Each leuco dye was separately physically spread onto a 1-inch square, thin plastic adhesive label (Zebra Technologies, Product # SAM5612, Z ultimate 3000T-white). The release liner was used to physically impregnate the colorless leuco dye powder onto the individual adhesive strip. These adhesive strips were affixed onto the bottom of a plastic bag (large enough so that the bag would fit over an adult shoe) such that the leuco dye powder would be exposed to any vegetation that came into contact with the plastic bag. The leuco dye impregnated plastic bags were placed over both shoes of a subject who then walked through a patch of vegetation known to contain poison ivy plants. After the walk, the adhesive strips were removed from the plastic bag and examined for visible color change. Each strip showed evidence of color development as follows: Pergascript Red-I-6B showed red streaks; Pergascript Green I-2G showed green spot color development; Copikem I yielded a blue color; Copikem 35 Magenta developed into magenta color and Copikem 4 Black showed black streaks.

The five different leuco dye impregnated plastic adhesive labels were used to detect the presence of poison ivy.

Example 3

Three hundred grams of sodium carbonate was dissolved in 1.8 liters of water. An article was soaked in the sodium carbonate solution for approximately 30 minutes, then hand squeezed to remove residual sodium carbonate.

Pergascript Red I-6B leuco dye was dissolved in a water miscible solvent such as ethanol, isopropyl alcohol or acetone at a concentration of approximately 5 mg of leuco dye per mL solvent. The sodium carbonate treated article was then placed in the colorless dye solution for approximately 15 minutes, removed, rinsed in water and air-dried. The dried article remained colorless.

Articles treated with a leuco dye included, fabric from cotton (100%) T-shirt, fabric from cotton (70%)/polyester (30%) T-shirt fabric, canvas work gloves and cotton gloves.

Example 4

Fabric from cotton (100%) T-shirt was treated with Pergascript Red I-6B dissolved in acetone or isopropyl alcohol as solvent as described in Example 3. Approximately 5 μL, of free flowing 2-deoxy urushiol liquid (prepared as described in Example 1) or purified poison oak extract were placed on each fabric resulting in an instantaneous red color.

Fabric impregnated with Pergascript Red I-6B (prepared as described in Example 3) was washed with aqueous laundry detergent and sodium hypochlorite bleached and then dried. The dried, washed fabric was treated with free flowing 2-deoxy urushiol liquid as described above and showed an instantaneous red color on exposure to 2-deoxy urushiol liquid.

An article, such as fabric, impregnated with a leuco dye can be used to detect the presence of an urushiol compound or poison oak extract.

Example 5

A cotton (100%) fabric wipe impregnated with Pergascript Red I-6B (prepared as described in Example 3) was used to locate and identify a poison sumac plant at a local arboretum containing numerous plants of various species. Visual identity of the poison sumac plant was previously unknown to the investigator. Each plant in an approximately 30×30 foot grid was tested by rubbing a leaf or breaking off a leaf stem and rubbing the broken stem on the wipe. After testing approximately 15 different green plants a poison sumac plant was instantaneously identified by the development of the red-magenta color on the Pergascript Red I-6B impregnated cotton fabric wipe.

Example 6

A cotton (100%) fabric wipe impregnated with Pergascript Red I-6B (prepared as described in Example 3) was used to determine the presence of an urushiol compound in several plants. 22 different plants were tested as described in Example 5. Table 3 lists the common names and scientific name of the plant and if a color changed occurred after contact with a cotton fabric wipe impregnated with Pergascript Red I-6B.

TABLE 3

| Common name of plant | Scientific name of plant | Color change |
|---|---|---|
| Sweet Basil | Ocimum basilicum | No |
| French Lavender | Lavandula stoechas | No |
| Common Lilac | Syringa vulgaris | No |
| Rhododendron | Rhododendron catawbiense | No |
| Rose, Red Eden | Rosa meridrason | No |
| Fern, broad beechfern | Phegopteris hexagonoptera | No |
| Peony | Paeonia hybrids | No |
| Tiger Lily | Lilium lancifolium | No |
| Rosemary | Rosemaryinus officinalis | No |
| Hydrangea | Hydrangea macrophylla | No |
| Sugar Maple | Acer saccharum | No |
| Bradford Pear Tree | Pyrus calleryana 'Bradford' | No |
| Cortland Apple Tree | Malus 'Cortland" | No |
| Elm, American | Ulmus 'Americana' | No |
| Mint | Mentha × piperita | No |
| Oregano | Origanum vulgare | No |
| Rhubarb | Rheum rhabarbarum | No |
| Marigolds | Tagetes patula | No |
| Mother in law's tongue | Sansevieria trifasciata | No |
| Poison Sumac | Toxicodendron vernix | Yes, red |
| Poison Ivy | Toxicodendron radicans | Yes, red |
| Poison Oak Extract | Toxicodendron pubescens | Yes, red |

As shown in Table 3 the poison sumac, poison ivy, and poison oak extract were the only species that resulted in a visible color of the wipe. These 3 plants are known to contain urushiol compounds.

Example 7

White cotton work gloves were treated with Pergascript Red I-6B as described in Example 3. The gloves were donned by an investigator, and various plants, excluding poison ivy, in the neighborhood were picked and handled, with no evidence of dye turn-on. When poison ivy plants (leaves, stems and roots) were pulled, the glove palms immediately turned red.

Work gloves treated with a leuco dye are a convenient means of detecting the presence of a polyhydroxyaromatic skin irritant found in the sap of plants while gardening.

Example 8

Three grams of sodium carbonate was dissolved in approximately 15 mL of water. Two 3-inch square cotton cloths were soaked in the sodium carbonate solution for 30 minutes then removed from the sodium carbonate solution and hand squeezed to remove excess aqueous solution.

Pergascript Red I-6B leuco dye (10.4 mg) was dissolved in denatured alcohol (11 mL, Klean-Strip, WM Barr, Memphis, Tenn.) containing 40-50% ethyl alcohol, 50-55% methyl alcohol, 1-4% methyl isobutyl ketone, 0.5-1.5% ethyl acetate, and 0.5-1.5% heptane. The two 3-inch sodium carbonate treated cloths were soaked in the Pergascript Red I-6B denatured alcohol solution for approximately 15 minutes, removed, rinsed in water and air-dried. The dried cloths remained colorless.

Approximately 5 µL of free flowing 2-deoxy urushiol liquid (prepared as described in Example 1) was applied to each cloth resulting in an instantaneous red/magenta color change at the site of application.

Example 9

Pergascript Red I-6B and Copikem 35 Magenta were mixed as dry powders in ratios of 2:1, 1:1 or 1:2, and the dry powder mixtures were separately added to denatured ethanol in a quantity in excess of solubility. Swatches of sodium carbonate treated fabric, prepared as described in Example 3, were soaked in the mixed dye solutions for approximately 15 minutes, removed, rinsed in water and air-dried. The dried fabric swatches remained colorless.

When each of the dried fabric swatches impregnated with a mixture of the leuco dyes were touched with a small amount of free-flowing 2-deoxyurushiol liquid (prepared as described in Example 1), the swatches instantly turned red at the point of contact with the 2-deoxyurushiol. When taken into the field and challenged with living and dead poison ivy, the swatches instantly indicated the exposure to a polyhydoxyaromatic skin irritant by an instanteous color change.

The results show that a mixture of leuco dyes can be used to detect the exposure to a polyhydroxyaromatic skin irritant.

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for detecting exposure to a polyhydoxyaromatic skin irritant found in the sap of a plant comprising contacting an article comprising a colorless leuco dye with the polyhydroxyaromatic skin irritant in the sap of the plant or on a subject wherein the colorless leuco dye is 1(3H)-isobenzofuranone,3,3-bis(2-methyl-1-octyl-1H-indol-3-yl)-, spiro[isobenzofuran-1(3H),9'-[9H]xanthen]-3-one,2'-[bis(phenylmethyl)amino]-6'-(diethylamino)-, 1(3H)-isobenzofuranone,6-(dimethylamino)-3,3-bis[4-(dimethylamino)phenyl]-, 3-[butyl-2-methylindol-3-yl]-3-(1-octyl-2-methylindol-3-yl)-1(3H)isobenzofuranone or 3-diethylamino-6-methyl-7-anilinofluoran, wherein the colorless leuco dye undergoes an instantaneous visual color change, wherein the instantaneous visual color change of the colorless leuco dye serves as an indicator that exposure to the polyhydroxyaromatic skin irritant has occurred.

2. The method of claim 1, wherein the plant is poison ivy, poison oak, Rocky Mountain poison oak, poison sumac, poison dogwood, a Japanese or Asian lacquer tree, a mango tree, a cashew tree, a Rengas tree, a Burmese lacquer tree, a Caribbean shrub, an India marking nut tree, *Ginkgo biloba*, or a tree of the Proteaceae family.

3. The method of claim 2, wherein the plant is poison ivy, poison oak, poison sumac poison dogwood, a mango tree, a cashew tree or a lacquer tree.

4. The method of claim 1, wherein the leuco dye is colorless and undergoes an instantaneous visible color change on contact with the polyhydroxyaromatic skin irritant.

5. The method of claim 1, wherein the leuco dye is 1(3H)-isobenzofuranone,3,3-bis(2-methyl-1-octyl-1H-indol-3-yl)-.

6. The method of claim 1, wherein the color change is a visible color change from a colorless form of the leuco dye to a colored form of the leuco dye.

7. The method of claim 1, wherein the polyhydoxyaromatic skin irritant found in the sap of the plant is an urushiol compound.

8. A method for detecting exposure to a polyhydoxyaromatic skin irritant found in the sap of poison ivy, poison oak, poison sumac, poison dogwood, a mango tree, a cashew tree or a lacquer tree comprising contacting an article comprising colorless 1(3H)-isobenzofuranone,3,3-bis(2-methyl-1-octyl-1H-indol-3-yl)- with the polyhydroxyaromatic skin irritant in the sap or on a subject, wherein the colorless 1(3H)-isobenzofuranone,3,3-bis(2-methyl-1-octyl-1H-indol-3-yl)-undergoes an instantaneous visible color change, wherein the instantaneous visible color change serves as an indicator that exposure to a polyhydroxyaromatic skin irritant has occurred.

* * * * *